United States Patent
Hur et al.

(10) Patent No.: US 9,346,772 B2
(45) Date of Patent: May 24, 2016

(54) PREPARATION METHOD FOR AN IMINE COMPOUND AND REDUCTION METHOD FOR SOLID POWDER OF A CARBAMIC ACID DERIVATIVE

(71) Applicant: Sogang University Research Foundation, Seoul (KR)

(72) Inventors: Nam Hwi Hur, Seoul (KR); Byeong No Lee, Yongin-si (KR)

(73) Assignee: Sogang University Research Foundation, Seoul (KR)

( * ) Notice: Subject to any disclaimer, the term of this patent is extended or adjusted under 35 U.S.C. 154(b) by 0 days.

(21) Appl. No.: 14/823,682

(22) Filed: Aug. 11, 2015

(65) Prior Publication Data

US 2015/0344451 A1 Dec. 3, 2015

Related U.S. Application Data

(60) Division of application No. 14/567,333, filed on Dec. 11, 2014, now Pat. No. 9,126,903, which is a continuation-in-part of application No. 13/967,036, filed on Aug. 14, 2013, now abandoned, which is a continuation of application No. PCT/KR2012/001046, filed on Feb. 13, 2012.

(30) Foreign Application Priority Data

Feb. 14, 2011 (KR) .................. 10-2011-0012972

(51) Int. Cl.
| | |
|---|---|
| C07D 295/13 | (2006.01) |
| C07B 43/00 | (2006.01) |
| C07C 269/04 | (2006.01) |
| C07C 249/02 | (2006.01) |
| C07C 209/62 | (2006.01) |
| C07C 209/46 | (2006.01) |
| C07C 209/00 | (2006.01) |

(52) U.S. Cl.
CPC .............. *C07D 295/13* (2013.01); *C07B 43/00* (2013.01); *C07C 209/00* (2013.01); *C07C 209/46* (2013.01); *C07C 209/62* (2013.01); *C07C 249/02* (2013.01); *C07C 269/04* (2013.01)

(58) Field of Classification Search
CPC .... C07D 295/13; C07B 43/00; C07C 269/04; C07C 249/02; C07C 209/62; C07C 209/46
See application file for complete search history.

(56) References Cited

U.S. PATENT DOCUMENTS 2,927,129 A * 3/1960 Hennig ................ B01J 19/0013
562/550
7,186,844 B2 3/2007 Ikemoto

FOREIGN PATENT DOCUMENTS

| JP | 06-345708 | 12/1994 |
|---|---|---|
| JP | 2000-504688 | 4/2000 |

OTHER PUBLICATIONS

International Search Report issued in International App. No. PCT/KR2012/001046, mailed Sep. 28, 2012.
Mitewa et al.; "Spectroscopic and Quantum Chemical Study of the Structure of a New Paramagnetic Dimeric Palladium (II, III) Complex with Creatine"; Journal of Molecular Structure; 609 (1-3), 61-65; 2002.

* cited by examiner

*Primary Examiner* — Erich A Leeser
(74) *Attorney, Agent, or Firm* — Greer Burns & Crain Ltd.

(57) ABSTRACT

The present application relates to a preparation method for solid powder of a carbamic acid derivative, which includes reacting an amine derivative with carbon dioxide at a temperature in a range of from about −30° C. to about 500° C. and at a pressure in a range of from about 0.3 MPa to about 100 MPa. In addition, the present disclosure relates to a reduction method for solid powder of a carbamic acid derivative to an amine derivative and carbon dioxide, which includes dissolving solid powder of the carbamic acid derivative prepared in a solvent; refluxing the carbamic acid derivative at a temperature in a range of from about 30° C. to about 100° C.; and evaporating the solvent.

5 Claims, 1 Drawing Sheet

PREPARATION METHOD FOR AN IMINE COMPOUND AND REDUCTION METHOD FOR SOLID POWDER OF A CARBAMIC ACID DERIVATIVE

CROSS-REFERENCE TO RELATED APPLICATIONS

This application is a divisional application of U.S. patent application Ser. No. 14/567,333 filed on Dec. 11, 2014, which is a continuation-in-part of U.S. patent application Ser. No. 13/967,036 filed on Aug. 14, 2013, which is a continuation of International Application No. PCT/KR/2012/001046 filed on Feb. 13, 2012.

TECHNICAL FIELD

The embodiments described herein pertain generally to a preparation method for solid powder of a carbamic acid derivative and a reduction method for the solid powder of a carbamic acid derivative, and more specifically, to a preparation method for the solid powder of the carbamic acid derivative through a reaction between an amine derivative with carbon dioxide, and a reduction method for the solid powder of the carbamic acid derivative to the amine derivative and the carbon dioxide.

BACKGROUND

An amine compound refers to a compound, such as an ammonia molecule, containing a nitrogen atom having an unshared electron pair and is typically basic. Such an amine compound has been found from both plants and animals. Amine compounds extracted from plants include nicotine contained in tobacco and cocaine which can cause hallucination. Many of daily used drugs contain an amine functional group. A typical drug is penicillin. Further, dopamine well known as a material that stimulates brain nerves and phenylethylamine as a main substance of chocolate are typical compounds each containing an amine functional group. In many cases, amine compounds each having a relatively small molecular weight exist in a liquid-phase form at room temperature under atmospheric pressure, give out smell of fish, and cause skin allergies. Further, such liquid amines easily react with oxygen or the like in the air so as to be changed, and, thus, if they are not completely sealed, it is difficult to maintain purity thereof. Therefore, liquid amines are difficult to handle and store and are limited in applications thereof.

As a method for solving the above problem, a solid amine salt prepared by reacting an amine with an acid has been used in substitution for amine. Such an amine salt is prepared as a solid salt by adding a strong acid such as sulfuric acid or hydrochloric acid to a liquid amine with a precipitation reaction. By way of example, when a hydrochloric acid solution is put into phenylethylamine, a precipitation reaction occurs in an instant with conversion into phenylethylamine hydrochloric acid which has been actually used in substitution for liquid amine. Such solid amine salts exist in a stable solid form at room temperature and have characteristics similar to those of liquid amines when they are dispersed in a solution and react with other compounds. Further, such salts have a very high solubility to water and are useful for utilizing amine. In particular, a drug containing an amine functional group which is not dissolved well in water due to its high molecular weight is used as being bonded to an acid such as hydrochloric acid. This is because if the drug is converted into a salt, solubility is sharply increased in an aqueous solution and thus the drug is suitable for use as a drug.

However, such amine salts need a solvent when being generated, the solvent needs to be removed after a reaction due to unnecessary materials added to generate the salts, and an additional process for removing a remaining material is needed. Further, a neutralization process for removing a strong acid such as hydrochloric acid or sulfuric acid used in a process for preparing an amine salt is essential. Such a multistep process causes environmental pollution.

As described above, as one of alternatives to solve such problems of the liquid amine and the solid amine salt, there is a method for preparing solid amine derivatives from a liquid amine by using eco-friendly carbon dioxide as a reactant. If a reaction is made between a liquid amine and carbon dioxide, the carbon dioxide is generally inserted into N—H bonds of amine molecules and converted into carbamic acid derivatives. Most of these carbamic acid derivatives exist in a stable solid form in the air. Further, they can be easily separated into the amine and the carbon dioxide by a slight external change, and, thus, they can act as a good alternative to solve the problems of the liquid amine and the solid amine salt.

Many methods for preparing new compounds using carbon dioxide as a reactant have been known so far, and various methods for preparing new compounds by the methods have been reported [Sakakura, T.; Choi, J.-C.; Yasyda, H., Chem. Rev., 2007, 107, 2365]. Further, it is known that carbamic acid derivatives can be formed by a reaction between an amine and carbon dioxide. However, in most of the conventionally known reactions between an amine and carbon dioxide, while carbon dioxide gas is discharged under atmospheric pressure for a long time by using a solvent, a compound is formed in a reactor and used, without an additional separation process, for an intermediate step in a process for forming another compound, or a compound is used for synthesizing a compound in a gel form (U.S. Pat. No. 3,551, 226), or there are known researches in which a compound is formed by using a polar solvent as an ionic liquid [1) Jessop, P. G.; Heldebrant, D. J.; Li, X.; Eckert, C. A.; Liotta, C. L., Nature, 2005, 436, 1102, 2) Lam Phan; Andreatta J. R.; Horvey, L. K.; Edie, C. F.; Luco. Aimé e-L.; Mirchandani, A.; Darensbourg, D. J.; Jessop, P. G., J. Org. Chem., 2008, 73, 127-132, 3) Liu, Y.; Tang, Y.; Barashkov, N. N.; Irgibaeva, I. S.; Y. Lam, J.; Hu, W. R.; Birimzhanova, D.; Yu, Y.; Tang, B. Z., J. Am. Chem. Soc., 2010, 132, 13951].

In U.S. Pat. No. 3,551,226, it is disclosed that liquid amines react with carbon dioxide under atmospheric pressure at a low temperature for a long time and are converted into and used as a gel type compound. Such a gel type compound contains amine and carbon dioxide at an irregular ratio and is a very sticky liquid, and, thus, it is difficult to separate the gel type compound into a pure solid amine in powder form by a typical drying method. Further, if an amine is solidified by using carbon dioxide under atmospheric pressure, a sticky gel type compound is obtained rather than a solid compound powder. As described above, it is known that carbamic acid derivatives can be formed by a reaction between an amine and carbon dioxide. However, there is no research result regarding a separation or preparation method for a solid carbamic acid derivative in powder form.

SUMMARY

In order to solve problems of an amine derivative in a liquid form at room temperature under atmospheric pressure, an objective of the present disclosure is to provide a preparation method for a carbamic acid derivative in solid powder form from a liquid amine derivative by using carbon dioxide as a reactant.

Further, another objective of the present disclosure is to provide a reduction method for the solid powder of the carbamic acid derivative to the liquid amine derivative and the carbon dioxide.

However, the problems sought to be solved by the present disclosure are not limited to the above description and other problems can be clearly understood by those skilled in the art from the following description.

In accordance with an aspect of the present disclosure, there is provided a preparation method for solid powder of a carbamic acid derivative, including: reacting an amine derivative with carbon dioxide at a temperature in a range of from about −30° C. to about 500° C. and at a pressure in a range of from about 0.3 MPa to about 100 MPa.

In accordance with another aspect of the present disclosure, there is provided a reduction method for solid powder of a carbamic acid derivative to an amine derivative and carbon dioxide, including: dissolving the solid powder of the carbamic acid derivative prepared by the preparation method of the present disclosure in a solvent; refluxing the carbamic acid derivative in the solvent at a temperature in a range of from about 30° C. to about 100° C.; and evaporating the solvent.

According to an example embodiment of the present disclosure, in a preparation method for solid powder of a carbamic acid derivative, an amine and carbon dioxide react with each other at a high pressure without using a solvent, and, thus, they can be easily converted into pure solid powder of a carbamic acid derivative without by-products, and time and energy required for solidification can be remarkably reduced. In the method according to an example embodiment of the present disclosure, an undiluted solution of a liquid amine can be used without using a solvent, and, thus, a very high productivity can be obtained in a relatively small reactor as compared with a case where a solvent is used. Further, remaining impurities contained in a liquid amine derivative can be minimized, and, thus, very pure solid powder of a carbamic acid derivative with few impurities or with substantially no impurities can be prepared.

In particular, the solid powder of the carbamic acid derivative prepared according to an example embodiment of the present disclosure exists in stable solid state at room temperature as compared with the liquid amine derivative. Thus, (1) an amine vapor is not produced so that the solid powder of the carbamic acid derivative is odorless; (2) the solid powder of the carbamic acid derivative is not easily oxidized in the air so that it is easy and safe to handle and use it; (3) the solid powder of the carbamic acid derivative can be easily separated into the amine and the carbon dioxide during the reaction so that it has a reactivity equivalent to that of the liquid amine derivative; (4) the solid powder of the carbamic acid derivative can be used in conditions without a solvent; (5) the solid powder of the carbamic acid derivative does not contain impurities, so that less by-products are produced through a side reaction; (6) general toxicities of the liquid amine derivative to humans are remarkably reduced; (7) the solid powder of the carbamic acid derivative is hardly inflammable; and (8) the solid powder of the carbamic acid derivative contains few impurities, so that it can be reduced to an amine derivative having a very high purity.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION

Hereinafter, example embodiments will be described in detail with reference to the accompanying drawings so that inventive concept may be readily implemented by those skilled in the art.

However, it is to be noted that the present disclosure is not limited to the example embodiments but can be realized in various other ways. In the drawings, certain parts not directly relevant to the description are omitted to enhance the clarity of the drawings, and like reference numerals denote like parts throughout the whole document.

Throughout the whole document of the present disclosure, the terms "connected to" or "coupled to" are used to designate a connection or coupling of one element to another element and include both a case where an element is "directly connected or coupled to" another element and a case where an element is "electronically connected or coupled to" another element via still another element.

Throughout the whole document of the present disclosure, the term "on" that is used to designate a position of one element with respect to another element includes both a case that the one element is adjacent to the another element and a case that any other element exists between these two elements.

Throughout the whole document of the present disclosure, the term "comprises" or "includes" and/or "comprising" or "including" used in the document means that one or more other components, steps, operations, and/or the existence or addition of elements are not excluded in addition to the described components, steps, operations and/or elements.

The terms "about", "approximately" or "substantially" used in this document are intended to have meanings close to numerical values or ranges specified with an allowable error and intended to prevent accurate or absolute numerical values disclosed for understanding of the present invention from being illegally or unfairly used by any unconscionable third party.

Throughout the whole document of the present disclosure, the term "step of" does not mean "step for."

Throughout the whole document of the present disclosure, the term "combinations thereof" included in Markush type description means mixture or combinations thereof one or more components, steps, operations and/or elements selected from the group consisting of components, steps, operation and/or elements described in Markush type and thereby means that the disclosure includes one or more components, steps, operations and/or elements selected from the Markush group.

Throughout the whole document of the present disclosure, the description "A and/or B" means "A or B, or A and B."

Throughout the whole document of the present disclosure, the term "alkyl group" may include linear or branched, saturated or unsaturated $C_{1-30}$ alkyl groups and may include, for example methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, eicosanyl, or all available isomers thereof, but the present disclosure may not be limited thereto.

Hereinafter, example embodiments of the present disclosure will be explained in detail, but the present disclosure may not be limited thereto.

In accordance with an aspect of the present disclosure, there is provided a preparation method for solid powder of a carbamic acid derivative, including: reacting an amine derivative with carbon dioxide at a temperature in a range of from about −30° C. to about 500° C. and at a pressure in a range of from about 0.3 MPa to about 100 MPa.

In accordance with an example embodiment of the present disclosure, the amine derivative may include an amine-based compound represented by the following Chemical Formula 1 or Chemical Formula 2, but may not be limited thereto:

[Chemical Formula 1]

[Chemical Formula 2]

wherein in Chemical Formulas 1 or 2, each of $R_1$, $R_2$, $R_3$ and $R_4$ is independently hydrogen; a $C_{1-30}$ alkyl group substituted or non-substituted with nitrogen; a phenyl group substituted or non-substituted with nitrogen; a $C_{6-30}$ aryl group substituted or non-substituted with nitrogen; or a $C_{3-30}$ cycloalkyl group substituted or non-substituted with nitrogen, and

$R_5$ is a $C_{2-30}$ alkyl group substituted or non-substituted with nitrogen; a phenyl group substituted or non-substituted with nitrogen; a $C_{6-30}$ aryl group substituted or non-substituted with nitrogen; or a $C_{3-30}$ cycloalkyl group substituted or non-substituted with nitrogen.

In accordance with an example embodiment of the present disclosure, the amine-based compound may include at least one primary or secondary amine group, but may not be limited thereto.

In accordance with an example embodiment of the present disclosure, the amine-based compound may include a liquid amine, but may not be limited thereto.

In accordance with an example embodiment of the present disclosure, the prepared carbamic acid derivative may include a compound represented by the following Chemical Formula 3, Chemical Formula 3', or Chemical Formula 4, but may not be limited thereto:

[Chemical Formula 3]

[Chemical Formula 3']

[Chemical Formula 4]

wherein in Chemical Formulas 3, 3', or 4, each of $R_1$, $R_2$, $R_3$, and $R_4$ is independently hydrogen; a $C_{1-30}$ alkyl group substituted or non-substituted with nitrogen; a phenyl group substituted or non-substituted with nitrogen; a $C_{6-30}$ aryl group substituted or non-substituted with nitrogen; or a $C_{3-30}$ cycloalkyl group substituted or non-substituted with nitrogen, and $R_5$ is a $C_{2-30}$ alkyl group substituted or non-substituted with nitrogen; a phenyl group substituted or non-substituted with nitrogen; a $C_{6-30}$ aryl group substituted or non-substituted with nitrogen; or a $C_{3-30}$ cycloalkyl group substituted or non-substituted with nitrogen.

The compound represented by Chemical Formula 3' may be the same or substantially same as the compound represented by Chemical Formula 3.

In accordance with an example embodiment of the present disclosure, a content of an amine group (—NH) in the amine derivative may be from about 5 wt % to about 99 wt %, but may not be limited thereto.

In accordance with an example embodiment of the present disclosure, the temperature may be in a range of from about −30° C. to about 500° C., but may not be limited thereto. During the reaction, if the temperature is too low or too high, a system or costs may be unnecessarily consumed to maintain a low temperature or a high temperature. By way of example, the temperature may be in a range of from about −30° C. to about 500° C., from about −30° C. to about 400° C., from about −30° C. to about 300° C., from about −30° C. to about 200° C., from about −30° C. to about 100° C., from about −30° C. to about 50° C., from about −30° C. to about 30° C., from about −30° C. to about 20° C., from about −30° C. to about 10° C., from about −30° C. to about 0° C., from about −30° C. to about −10° C., from about −30° C. to about −20° C., from about −20° C. to about 500° C., from about −10° C. to about 500° C., from about 0° C. to about 500° C., from about 10° C. to about 500° C., from about 20° C. to about 500° C., from about 30° C. to about 500° C., from about 50° C. to about 500° C., from about 100° C. to about 500° C., from about 200° C. to about 500° C., from about 300° C. to about 500° C., from about 400° C. to about 500° C., or from about 0° C. to about 300° C., but the present disclosure may not be limited thereto.

In accordance with an example embodiment of the present disclosure, the pressure may be in a range of from about 0.3 MPa to about 100 MPa, but may not be limited thereto. During the reaction, if the pressure is less than about 0.3 MPa, solid powder of a carbamic acid derivative may not be formed and a gel type compound may be formed. By way of example, the pressure may be in a range of from about 0.3 MPa to about 100 MPa, from about 0.3 MPa to about 90 MPa, from about 0.3 MPa to about 80 MPa, from about 0.3 MPa to about 70 MPa, from about 0.3 MPa to about 60 MPa, from about 0.3 MPa to about 50 MPa, from about 0.3 MPa to about 40 MPa, from about 0.3 MPa to about 30 MPa, from about 0.3 MPa to about 20 MPa, from about 0.3 MPa to about 10 MPa, from about 0.3 MPa to about 5 MPa, from about 0.3 MPa to about 1 MPa, from about 1 MPa to about 100 MPa, from about 5 MPa to about 100 MPa, from about 10 MPa to about 100 MPa, from about 20 MPa to about 100 MPa, from about 30 MPa to about 100 MPa, from about 40 MPa to about 100 MPa, from about 50 MPa to about 100 MPa, from about 60 MPa to about 100 MPa, from about 70 MPa to about 100 MPa, from about 80 MPa to about 100 MPa, from about 90 MPa to about 100 MPa, or from about 1 MPa to about 50 MPa, but the present disclosure may not be limited thereto.

The reaction may be made by adding the carbon dioxide to the amine derivative, and even when the carbon dioxide is added to an additional solvent besides the amine derivative, pure solid powder of a carbamic acid derivative can be prepared in an equivalent manner to a case where the amine derivative reacts with the carbon dioxide without a solvent.

In accordance with an example embodiment of the present disclosure, the preparation method for solid powder of the carbamic acid derivative may include reacting a mixed solution of the amine derivative and one or more selected from the group consisting of ethers, alcohols, aliphatic hydrocarbons, carbocycles, heterocycles, aromatics, substituted heteroaromatic cycles, and so on, with the carbon dioxide, but may not be limited thereto. As described above, if an additional solvent is input besides the amine derivative, a content of the amine derivative in the mixed solution may be from about 1 wt % to about 99 wt %, for example, from about 1 wt % to about 99 wt %, from about 1 wt % to about 90 wt %, from about 1 wt % to about 80 wt %, from about 1 wt % to about 70 wt %, from about 1 wt % to about 60 wt %, from about 1 wt % to about 50 wt %, from about 1 wt % to about 40 wt %, from about 1 wt % to about 30 wt %, from about 1 wt % to about 20 wt %, from about 1 wt % to about 10 wt %, from about 1 wt % to about 5 wt %, from about 5 wt % to about 99 wt %, from about 10 wt % to about 99 wt %, from about 20 wt % to about 99 wt %, from about 30 wt % to about 99 wt %, from about 40 wt % to about 99 wt %, from about 50 wt % to about 99 wt %, from about 60 wt % to about 99 wt %, from about 70 wt % to about 99 wt %, from about 80 wt % to about 99 wt %, or from about 90 wt % to about 99 wt %, but the present disclosure may not be limited thereto.

In accordance with an example embodiment of the present disclosure, in the preparation method for the solid powder of the carbamic acid derivative, the method may further include, after the reaction with the carbon dioxide, reducing the pressure to be in a range of from about 0.01 MPa to about 0.1 MPa so as to evaporate excess carbon dioxide, but the present disclosure may not be limited thereto.

In accordance with an example embodiment of the present disclosure, in the preparation method for solid powder of the carbamic acid derivative, the method may further include washing the prepared solid powder of the carbamic acid derivative by using $C_1$-$C_{12}$ alcohols, tetrahydrofuran, ethers, dimethylformamide, or mixed solutions thereof, and drying the solid powder of the carbamic acid derivative, but the present disclosure may not be limited thereto. If the method further includes the washing and drying step, impurities in the amine derivative are removed and solid powder of the carbamic acid derivative having a high purity can be prepared.

In accordance with an example embodiment of the present disclosure, the carbon dioxide may include carbon dioxide in a gas-phase, carbon dioxide in a liquid-phase, carbon dioxide in a supercritical state, or solid-phase dry ice, but the present disclosure may not be limited thereto.

In accordance with another aspect of the present disclosure, there is provided a reduction method for solid powder of a carbamic acid derivative, the method including: dissolving the solid powder of the carbamic acid derivative prepared by the method of the above-described aspect of the present disclosure in a solvent; refluxing the carbamic acid derivative in the solvent at a temperature in a range of from about 30° C. to about 100° C.; and evaporating the solvent to obtain an amine derivative and carbon dioxide.

In accordance with an example embodiment of the present disclosure, the solvent is not particularly limited as long as it can dissolve a solid-state carbamic acid derivative and can be easily separated from the prepared amine derivative and may include, for example, $C_1$-$C_{12}$ alcohols, $C_2$-$C_{12}$ ethers, and the like, but may not be limited thereto.

In accordance with an example embodiment of the present disclosure, the temperature may be in a range of from about 30° C. to about 100° C., from about 30° C. to about 90° C., from about 30° C. to about 80° C., from about 30° C. to about 70° C., from about 30° C. to about 60° C., from about 30° C. to about 50° C., from about 30° C. to about 40° C., from about 40° C. to about 100° C., from about 50° C. to about 100° C., from about 60° C. to about 100° C., from about 70° C. to about 100° C., from about 80° C. to about 100° C., from about 90° C. to about 100° C., or from about 50° C. to about 80° C., but the present disclosure may not be limited thereto.

In accordance with another aspect of the present disclosure, there is provided a preparation method for an imine compound, the method including: reacting the solid powder of the carbamic acid derivative prepared by the preparation method of the above-described aspect of the present disclosure with an aldehyde to obtain an imine compound.

In accordance with an example embodiment of the present disclosure, the solid powder of the carbamic acid derivative may include a compound represented by the following Chemical Formula 3, Chemical Formula 3', or Chemical Formula 4, but may not be limited thereto:

[Chemical Formula 3]

[Chemical Formula 3']

[Chemical Formula 4]

wherein in Chemical Formulas 3, 3', or 4, each of $R_1$, $R_2$, $R_3$ and $R_4$ is independently hydrogen; a $C_{1-30}$ alkyl group substituted or non-substituted with nitrogen; a phenyl group substituted or non-substituted with nitrogen; a $C_{6-30}$ aryl group substituted or non-substituted with nitrogen; or a $C_{3-30}$ cycloalkyl group substituted or non-substituted with nitrogen, and $R_5$ is a $C_{2-30}$ alkyl group substituted or non-substituted with nitrogen; a phenyl group substituted or non-substituted with nitrogen; a $C_{6-30}$ aryl group substituted or non-substituted with nitrogen; or a $C_{3-30}$ cycloalkyl group substituted or non-substituted with nitrogen.

The compound represented by Chemical Formula 3' may be the same or substantially same as the compound represented by Chemical Formula 3.

In accordance with an example embodiment of the present disclosure, any compound containing an aldehyde group may be used for the aldehyde without limitation. For, example, the aldehyde may include a $C_1$-$C_{12}$ compound containing an aldehyde group such as an $C_1$-$C_{12}$ alkyl aldehyde, or an $C_6$-$C_{12}$ arylaldehyde without limitation.

In accordance with an example embodiment of the present disclosure, the reaction between the solid powder of the carbamic acid derivative and the aldehyde may be carried out with no solvent or in the presence of a solvent.

In accordance with an example embodiment of the present disclosure, as the solvent in the reaction of the solid powder of the carbamic acid derivative and the aldehyde, any solvent, which can dissolve a solid-state carbamic acid derivative and be easily separated from an imine compound to be prepared, may be used without limitation, and for example, the solvent may include $C_1$-$C_{12}$ alcohols, or $C_2$-$C_{12}$ ethers and others, but not be limited thereto.

In accordance with an example embodiment of the present disclosure, the temperature may be in a range of from about 30° C. to about 100° C., from about 30° C. to about 90° C., from about 30° C. to about 80° C., from about 30° C. to about 70° C., from about 30° C. to about 60° C., from about 30° C. to about 50° C., from about 30° C. to about 40° C., from about 40° C. to about 100° C., from about 50° C. to about 100° C., from about 60° C. to about 100° C., from about 70° C. to about 100° C., from about 80° C. to about 100° C., from about 90° C. to about 100° C., or from about 50° C. to about 80° C., but may not be limited thereto.

Hereinafter, the present invention will be explained in detail with reference to examples. However, it is clear that the following examples are provided to illustrate the present invention but not to limit the present invention.

EXAMPLES

Example 1

3 g (50.0 mmol) of ehtylenediamine ($H_2NCH_2CH_2NH_2$) was put into a high-pressure reactor (Parr 4714) with a volume of 45 mL without a solvent and reacted at a carbon dioxide pressure of 3 MPa at a temperature of 50° C. for 5 hours so as to obtain a solid ehtylenediamine derivative. By putting the high-pressure reactor in an oil bath, the temperature was adjusted. After the reaction, remaining carbon dioxide was removed, and a remaining solid was washed by using 20 mL of ethanol and 20 mL of diethylether about five times and dried in a vacuum for about 3 hours so as to obtain solid powder of a carbamic acid derivative.

In order to confirm characteristics of the obtained solid powder, elemental analysis and nuclear magnetic resonance (NMR) spectroscopy analysis were carried out. According to results of the elemental analysis and the nuclear magnetic resonance spectroscopy analysis, it was confirmed that the obtained solid powder was a 2-aminoethyl carbamic acid compound represented as a chemical formula of $H_3N^+CH_2CH_2NHCOO^-$. A yield of the obtained $H_3N^+CH_2CH_2NHCOO^-$ was 98% or more based on the used ehtylenediamine.

The results of the elemental analysis (unit: %) and the $^1H$ NMR analysis on the $H_3N^+CH_2CH_2NHCOO^-$ as a product were as follows:

Elemental analysis (calculated value, experimental value): C, (34.61, 34.68), H, (7.75, 7.71), N, (26.91, 26.93);

$^1H$ NMR (400 MHz, $CD_3OD$, 27° C.) δ=4.659 (s, 3H, —$NH_3$), 3.005 (t, 2H, —$CH_2NHCOO$—), 2.765 (t, 2H, —$CH_2NH_3$), 2.681 (s, 1H, —NH).

Comparative Example 1

Comparative Example 1 was carried out in the same manner as Example 1 except that 3 g (50.0 mmol) of ehtylenediamine was used and carbon dioxide was bubbled under atmospheric pressure at a temperature of 0° C. for 16 hours.

In this case, the ehtylenediamine was converted into a transparent gel type compound having a very high viscosity, but solids were not produced. This result is the same as disclosed in U.S. Pat. No. 3,551,226, and it is determined that not a single pure product but a mixed unpure product was synthesized.

Example 2

Example 2 was carried out in the same manner as Example 1 except that diethylether (2 mL) was used as a solvent and 2 g (33.3 mmol) of ehtylenediamine was used so as to obtain solid powder of a carbamic acid derivative. In order to confirm characteristics of the obtained solid powder of the carbamic acid derivative, an elemental analysis and a nuclear magnetic resonance spectroscopy analysis were carried out in the same manner as Example 1.

A result of the elemental analysis (unit: %) on the obtained solid powder was almost the same as that of Example 1, and a result of the $^1H$ NMR analysis was exactly the same as that of Example 1. A yield of a product was 98% or more based on the used ehtylenediamine. According to the results of the elemental analysis and the $^1H$ NMR analysis, it was confirmed that the powder prepared in Example 2 was $H_3N^+CH_2CH_2NHCOO^-$ as the same material as that of Example 1.

Example 3

Example 3 was carried out in the same manner as Example 1 except that 10 g of solid-phase carbon dioxide (dry ice) was used as a source of carbon dioxide instead of gas-phase carbon dioxide and reacted with ehtylenediamine so as to obtain solid powder of a carbamic acid derivative. In order to confirm characteristics of the obtained solid powder of the carbamic acid derivative, an elemental analysis and a nuclear magnetic resonance spectroscopy analysis were carried out in the same manner as Example 1.

According to the results of the elemental analysis and the $^1H$ NMR analysis on the obtained solid powder, it was confirmed that the powder prepared in Example 3 was $H_3N^+CH_2CH_2NHCOO^-$ as the same material as that of Example 1.

Example 4

Example 4 was carried out in the same manner as Example 1 except that at a temperature of 25° C., 3 g (52.5 mmol) of allylamine ($CH_2$=$CHCH_2NH_2$) was used as a reactant instead of ehtylenediamine so as to obtain solid powder of a carbamic acid derivative. In order to confirm characteristics of the obtained solid powder of the carbamic acid derivative, an elemental analysis was carried out in the same manner as Example 1.

According to the results of the elemental analysis and a mass spectrometric analysis, it was confirmed that the obtained solid powder was prop-2-en-1-aminium allylcarbamate [($CH_2$=$CHCH_2NH_2)_2CO_2$ or $CH_2$=$CHCH_2NH$—

$CO_2^-H_3N^+CH_2CH=CH_2$]. A yield of the obtained solid powder was 96% or more based on the used allylamine.

The result of the elemental analysis (unit: %) was as follows:

Elemental analysis (calculated value, experimental value): C, (53.14, 53.09), H, (8.92, 8.97), N, (17.71, 17.65).

Example 5

Example 5 was carried out in the same manner as Example 1 except that 3 g (28.0 mmol) of benzylamine ($C_6H_5CH_2NH_2$) was used as a reactant instead of ehtylenediamine so as to obtain solid powder of a carbamic acid derivative. In order to confirm characteristics of the obtained solid powder of the carbamic acid derivative, an elemental analysis was carried out in the same manner as Example 1.

According to the results of the elemental analysis and a mass spectrometric analysis, it was confirmed that the obtained solid powder was phenylmethanaminium benzylcarbamate [$(C_6H_5CH_2NH_2)_2CO_2$ or $C_6H_5CH_2NH—CO_2H_3N^+CH_2C_6H_5$]. A yield of the obtained solid powder was 98% or more based on the used benzylamine.

The result of the elemental analysis (unit: %) was as follows:

Elemental analysis (calculated value, experimental value): C, (69.74, 69.91), H, (7.02, 7.18), N, (10.85, 10.82).

Example 6

Example 6 was carried out in the same manner as Example 1 except that 3 g (15.2 mmol) of dibenzylamine [$(C_6H_5CH_2)_2NH$] was used as a reactant instead of ehtylenediamine so as to obtain solid powder of a carbamic acid derivative. In order to confirm characteristics of the obtained solid powder of the carbamic acid derivative, an elemental analysis was carried out in the same manner as Example 1.

According to the results of the elemental analysis and a mass spectrometric analysis, it was confirmed that the obtained solid powder was dibenzylammonium dibenzylcarbamate [$\{(C_6H_5CH_2)_2NH\}_2CO_2$ or $(C_6H_5CH_2)_2NH—CO_2^-H_2N^+(CH_2C_6H_5)_2$]. A yield of the obtained solid powder was 98% or more based on the used dibenzylamine.

The result of the elemental analysis (unit: %) was as follows:

Elemental analysis (calculated value, experimental value): C, (79.42, 79.45), H, (6.90, 7.08), N, (6.39, 6.43).

Example 7

Example 7 was carried out in the same manner as Example 1 except that 3 g (14.9 mmol) of 1,4-(bis-aminopropyl)piperazine was used as a reactant instead of ehtylenediamine so as to obtain solid powder of a carbamic acid derivative. In order to confirm characteristics of the obtained solid powder of the carbamic acid derivative, an elemental analysis was carried out in the same manner as Example 1.

According to the results of the elemental analysis and a mass spectrometric analysis, it was confirmed that the obtained solid powder was 3-(4-(4-(carboxyamino)butyl)piperazin-1-yl)propan-1-aminium. A yield of the obtained solid powder was 98% or more based on the used 1,4-(bis-aminopropyl)piperazine.

The result of the elemental analysis (unit: %) was as follows:

Elemental analysis (calculated value, experimental value): C, (54.07, 54.37), H, (9.90, 10.10), N, (22.94, 23.18).

Example 8

Example 8 was carried out in the same manner as Example 1 except that 3 g (24.7 mmol) of phenylethylamine ($C_6H_5CH_2CH_2NH_2$) was used as a reactant instead of ehtylenediamine so as to obtain solid powder of a carbamic acid derivative. In order to confirm characteristics of the obtained solid powder of the carbamic acid derivative, an elemental analysis was carried out in the same manner as Example 1.

According to the results of the elemental analysis and a mass spectrometric analysis, it was confirmed that the obtained solid powder was 2-phenylethanaminium phenethylcarbamate. A yield of the obtained solid powder was 98% or more based on the used phenyl ethyl amine.

The result of the elemental analysis (unit: %) was as follows:

Elemental analysis (calculated value, experimental value): C, (71.30, 71.21), H, (7.74, 7.82), N, (11.17, 10.98).

Example 9

Example 9 was carried out in the same manner as Example 1 except that 3 g (41.0 mmol) of diethylamine [$(CH_3CH_2)_2NH$] was used as a reactant instead of ehtylenediamine so as to obtain solid powder of a carbamic acid derivative. In order to confirm characteristics of the obtained solid powder of the carbamic acid derivative, an elemental analysis was carried out in the same manner as Example 1.

According to the results of the elemental analysis and a mass spectrometric analysis, it was confirmed that the obtained solid powder was diethylammonium diethylcarbamate. A yield of the obtained solid powder was 93% or more based on the used diethylamine.

The result of the elemental analysis (unit: %) was as follows:

Elemental analysis (calculated value, experimental value): C, (56.80, 57.01), H, (11.65, 11.81), N, (16.82, 17.01).

A structure, a reaction time, and a yield of the solid powder of the solid carbamic acid derivatives produced from Examples 1 to 9 by reacting the amine with the carbon dioxides were as shown in the following Table 1.

TABLE 1

| | Amine derivative | Carbamic acid derivative | Temperature[a] (°C.) | Pressure (MPa) | Yield[b] (%) | Remarks |
|---|---|---|---|---|---|---|
| Example 1 | $H_2N\diagup\diagdown NH_2$ | $^+H_3N\diagup\diagdown\underset{H}{N}\diagdown COO^-$ | 50 | 3 | >98 | white powder |

TABLE 1-continued

| | Amine derivative | Carbamic acid derivative | Temperature[a] (°C) | Pressure (MPa) | Yield[b] (%) | Remarks |
|---|---|---|---|---|---|---|
| Comparative Example 1[c] | H₂N-CH₂CH₂-NH₂ | — | 0 | 0.1 | — | |
| Example 2[d] | H₂N-CH₂CH₂-NH₂ | ⁺H₃N-CH₂CH₂-NH-COO⁻ | 50 | 3 | >98 | white powder |
| Example 3[e] | H₂N-CH₂CH₂-NH₂ | ⁺H₃N-CH₂CH₂-NH-COO⁻ | 50 | 3 | >98 | white powder |
| Example 4 | allylamine | (allyl-NH₂)₂·CO₂ or allyl-NH-COO⁻ ⁺H₃N-allyl | 25 | 3 | >98 | white powder |
| Example 5 | benzylamine | (benzyl-NH₂)₂·CO₂ or benzyl-NH-COO⁻ ⁺H₃N-benzyl | 50 | 3 | >98 | needle crystal |
| Example 6 | (phenyl-CH₂-)₂NH | {((phenyl-CH₂-)₂NH₂)₂·CO₂} or (phenyl-CH₂-)₂NCOO⁻ H₂⁺N(-CH₂-phenyl)₂ | 50 | 3 | >98 | needle crystal |
| Example 7 | H₂N-(CH₂)₃-N(piperazine)N-(CH₂)₃-NH₂ | ⁺H₃N-(CH₂)₃-N(piperazine)N-(CH₂)₃-NH-COO⁻ | 50 | 3 | >98 | white crystalline |
| Example 8 | phenyl-CH₂CH₂-NH₂ | (phenyl-CH₂CH₂-NH₂)₂·CO₂ or phenyl-CH₂CH₂-NH-COO⁻ ⁺H₃N-CH₂CH₂-phenyl | 50 | 3 | >98 | white crystalline powder |
| Example 9 | azetidine (NH) | (azetidine-NH)₂·CO₂ or azetidine-N-COO⁻ H₂⁺N-azetidine | 50 | 3 | >95 | white powder[f] |

[a] Reaction time: 5 h, P_{CO2} = 3 MPa
[b] Isolation yield, no purification, based on amine
[c] CO₂: bubbling (1 atm)
[d] Di-ethyl ether: 2 mL
[e] Dry ice: 10 g
[f] Isolated at <10° C., unstable at >10° C.

Figure 1:
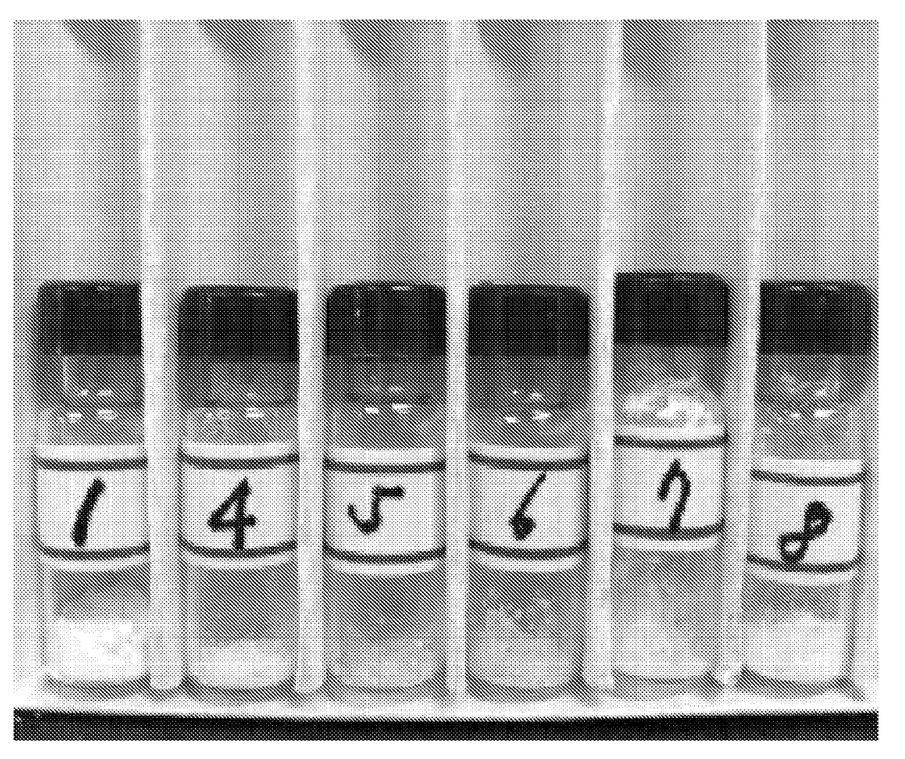
FIG. 1 provides a photo image of the solid powder of carbamic acid derivatives prepared in Example 1 and Examples 4 to 8 of the present disclosure.

Further, a photo image of the carbamic acid derivatives in solid powder form prepared in Example 1 and Examples 4 to 8 is shown in FIG. 1. As shown in FIG. 1, it was confirmed that a carbamic acid derivative in solid powder form is prepared according to the preparation method for solid powder of the carbamic acid derivative.

As described above, a solid-state carbamic acid derivative was synthesized from a liquid amine derivative. The following Examples 10 to 13 are examples showing that the solid powder of the carbamic acid derivatives prepared in Examples 1 to 9 had reactivities equivalent to that of a liquid amine derivative.

Example 10

Reduction of Solid Powder of the Carbamic Acid Derivative to Liquid Amine Derivative 1 g of 3-(4-(4-(carboxyamino)butyl)piperazin-1-yl)propan-1-aminium as the solid powder of the carbamic acid derivative prepared in Example 7 was dissolved in 3 mL of methanol as a solvent and refluxed at a temperature of from 65° C. to 70° C. for 2 hours. Then, a remaining solution was removed by depressurizing a pressure to 0.1 MPa at 0° C. and distilling the methanol so as to obtain a liquid compound. In order to confirm characteristics of the obtained liquid compound, an elemental analysis and a NMR analysis were carried out in the same manner as Example 1.

According to the results of the $^1$H NMR analysis and the elemental analysis, it was confirmed that the obtained liquid compound was 1,4-(bis-aminopropyl)piperazine which is the liquid amine derivative used as the reactant in Example 7. A yield of the obtained liquid compound was 98% or more based on the solid compound used in the present Example, and a purity of the obtained liquid compound was 99.8% or more.

Example 11

Reduction of Solid Powder of the Carbamic Acid Derivative to Liquid Amine Derivative 1 g of diethylammonium diethylcarbamate as the solid powder of the carbamic acid derivative prepared in Example 9 was dissolved in 3 mL of methanol as a solvent and refluxed at a temperature of from 60° C. to 65° C. for 2 hours. Then, a remaining solution was distilled under reduced pressure to 0.1 MPa at 0° C. so as to obtain a liquid compound. In order to confirm characteristics of the obtained liquid compound, an elemental analysis and a NMR analysis were carried out in the same manner as Example 1.

According to the results of the $^1$H NMR analysis and the elemental analysis, it was confirmed that the obtained liquid compound was diethylamine which is the liquid amine used as the reactant in Example 9. A yield of the obtained liquid compound was 95% or more based on the solid compound used in the present Example, and a purity of the obtained liquid compound was 99.9% or more.

Example 12

Reaction Between Solid Powder of the Carbamic Acid Derivative and Benzaldehyde 0.791 g (5 mmol) of prop-2-en-1-aminium allylcarbamate [$(CH_2$=$CHCH_2NH_2)_2CO_2$] as the solid powder of the carbamic acid derivative prepared in Example 4 was dissolved in 30 mL of ether as a solvent and reacted with 1.06 g (10 mmol) of benzaldehyde ($C_6H_5CHO$) and distilled under reduced pressure to 0.1 MPa so as to obtain a liquid compound. In order to confirm characteristics of the obtained liquid compound, a NMR analysis was carried out in the same manner as Example 1.

According to the result of the $^1$H NMR analysis, it was confirmed that the obtained liquid compound was N-benzylideneprop-2-en-1-amine. A yield of the obtained liquid compound was 97% or more based on the solid compound used in the present Example, and a purity of the obtained liquid compound was about 99.5%.

The result of the $^1$H NMR analysis was as follows:
$^1$H NMR (400 MHz, CDCl$_3$, 27° C.) δ=8.28 (s, 1H, CH=N), 7.76 (m, 2H, phenyl), 7.40 (m, 3H, phenyl), 6.07 (m, 1H, CH=CH$_2$), 5.23 (dd, 1H, CH$_{2a}$=), 5.14 (dd, 1H, CH$_{2b}$=), 4.25 (dd, 2H, CH$_2$—N).

Example 13

Reaction Between Solid Powder of the Carbamic Acid Derivative and Benzaldehyde

Example 13 was carried out in the same manner as Example 12 except that 0.57 g (10 mmol) of allylamine (CH$_2$=CHCH$_2$NH$_2$) was used instead of a solid carbamic acid derivative. After the reaction, a liquid compound was obtained through distillation under reduced pressure to 0.1 MPa. In order to confirm characteristics of the obtained liquid compound, a NMR analysis was carried out in the same manner as Example 1.

The obtained liquid compound was the same as the compound obtained in Example 12. A yield of the obtained liquid compound was 97% or more based on the allylamine used in the present Example, and a purity of the obtained liquid compound was about 99.3%.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the inventive concept is defined by the following claims and their equivalents rather than by the detailed description of the example embodiments. It shall be understood that all modifications and embodiments conceived from the meaning and scope of the claims and their equivalents are included in the scope of the inventive concept.

What is claimed is:

1. A preparation method for an imine compound, comprising:
    reacting an amine derivative with carbon dioxide at a temperature in a range of from about −30° C. to about 500° C. and at a pressure in a range of from about 0.3 MPa to about 100 MPa to obtain solid powder of a carbamic acid derivative; and
    reacting the solid powder of the carbamic acid derivative with an aldehyde to obtain an imine compound.

2. The preparation method for an imine compound of claim 1, wherein the reaction of the solid powder of the carbamic acid derivative with the aldehyde is performed without using a solvent.

3. The preparation method of claim 1, wherein the solid powder of the carbamic acid derivative includes a compound represented by the following Chemical Formula 3, Chemical Formula 3', or Chemical Formula 4:

[Chemical Formula 3]

[Chemical Formula 3']

[Chemical Formula 4]

wherein in Chemical Formulas 3, 3', or 4, each of $R_1$, $R_2$, $R_3$ and $R_4$ is independently hydrogen; a $C_{1-30}$ alkyl group substituted or non-substituted with nitrogen; a $C_{6-30}$ aryl group substituted or non-substituted with nitrogen; or a $C_{3-30}$ cycloalkyl group substituted or non-substituted with nitrogen, and $R_5$ is a $C_{2-30}$ alkyl group substituted or non-substituted with nitrogen; a $C_{6-30}$ aryl group substituted or non-substituted with nitrogen; or a $C_{3-30}$ cycloalkyl group substituted or non-substituted with nitrogen.

4. The preparation method of claim 1, wherein the aldehyde include a $C_1$-$C_{12}$ compound containing an aldehyde group.

5. The preparation method of claim 1, wherein the aldehyde is an $C_1$-$C_{12}$ alkyl aldehyde or an $C_6$-$C_{12}$ arylaldehyde.

* * * * *